United States Patent [19]

Wiese

[11] Patent Number: 5,227,156
[45] Date of Patent: Jul. 13, 1993

[54] USE OF ZINC COMPOUNDS TO STABILIZE A THIAZOLINONE PRESERVATIVE IN AN ANTI-DANDRUFF SHAMPOO

[75] Inventor: Robert S. Wiese, Grand Rapids, Mich.

[73] Assignee: Amway Corporation, Ada, Mich.

[21] Appl. No.: 869,548

[22] Filed: Apr. 14, 1992

[51] Int. Cl.[5] ............................................. A61K 7/075
[52] U.S. Cl. .................................... 424/70; 424/405; 424/642; 514/852
[58] Field of Search ........... 424/70, 642, 405, DIG. 4, 424/71; 514/188, 852

[56] References Cited

U.S. PATENT DOCUMENTS

| | | | |
|---|---|---|---|
| 3,236,733 | 2/1966 | Karsten | 514/188 |
| 3,785,985 | 1/1974 | Grand | 514/188 |
| 3,852,441 | 12/1974 | Kooistra, Jr. | 514/188 |
| 4,161,526 | 7/1979 | Gorman | 514/188 |
| 4,235,898 | 11/1980 | Watanabe et al. | 514/188 |
| 4,329,334 | 5/1982 | Su et al. | 424/71 |
| 4,379,753 | 4/1983 | Bolich, Jr. | 252/106 |
| 4,474,760 | 10/1984 | Hill | 424/76.8 |
| 4,482,715 | 11/1984 | Trotz et al. | 546/6 |
| 4,557,928 | 12/1985 | Glover | 424/70 |
| 4,581,351 | 4/1986 | Berke et al. | 424/63 |
| 4,654,213 | 3/1987 | Ramierez et al. | 514/335 |
| 4,822,511 | 4/1989 | Law | 424/70 |
| 4,835,149 | 5/1989 | Burke et al. | 514/188 |
| 5,015,415 | 5/1991 | Goze et al. | 424/70 |
| 5,057,153 | 10/1991 | Ruggiero | 514/500 |
| 5,098,473 | 3/1992 | Hani et al. | 106/18.33 |

OTHER PUBLICATIONS

Translation of Kokoju No. 60-41979, published Aug. 4, 1977.
Kathon CG/ICP, Kathon CG/ICP II Biocides, Rohm and Haas Company, 1987.
Kathon CG Microbicide, Cosmetics and Toiletries Rohm and Haas.

*Primary Examiner*—Thurman K. Page
*Assistant Examiner*—D. Colucci
*Attorney, Agent, or Firm*—Willian Brinks Olds Hofer Gilson & Lione

[57] ABSTRACT

The activity of a thiazolinone preservative, in an anti-dandruff shampoo containing pyrithione, is maintained by adding a stabilizer comprising a zinc compound.

9 Claims, 1 Drawing Sheet

USE OF ZINC COMPOUNDS TO STABILIZE A THIAZOLINONE PRESERVATIVE IN AN ANTI-DANDRUFF SHAMPOO

BACKGROUND OF THE INVENTION

This invention relates to anti-dandruff shampoos containing a preservative. In particular, it relates to the use of zinc compounds to stabilize the activity of a thiazolinone preservative added to an anti-dandruff shampoo containing zinc pyrithione.

It is known that microbiological contamination can result in poor shelf life and aesthetics of shampoos. Accordingly, preservatives are usually added to the shampoo composition during the manufacture of the shampoo to reduce or eliminate such contamination. One problem with adding a preservative to an anti-dandruff shampoo is that other ingredients present in the shampoo may react adversely with the preservative and reduce its activity. Specifically, it has been found that zinc pyrithione reacts adversely with some thiazolinone preservatives to reduce its activity and in turn its ability to prevent or reduce microbiological contamination.

Consequently, there is a need for an anti-dandruff shampoo having a stable active preservative. Surprisingly, it has been found that the activity of a thiazolinone preservative in an zinc pyrithione shampoo can be maintained by adding a stabilizer comprising a zinc compound.

The present invention thus provides a zinc pyrithione anti-dandruff shampoo having stable thiazolinone preservative.

SUMMARY OF THE INVENTION

An aqueous anti-dandruff shampoo is provided comprising up to about 40% surfactants; from about 0.1% to about 2.0% zinc pyrithione; from about 1 to about 30 parts per million ("ppm") of a preservative selected from the group consisting of 5-chloro-2-alkyl-4-isothiazolin-3-one, 2-alkyl-4-isothiazolin-3-one, and mixtures thereof; from about 0.001% to about 1.0% of a stabilizer comprising a zinc compound; miscellaneous optional ingredients; and water comprising the balance.

It is noted that, unless otherwise stated, all percentages given in this specification and the appended claims refer to percentages by weight.

DETAILED DESCRIPTION OF THE PREFERRED EMBODIMENTS

Figure 1:
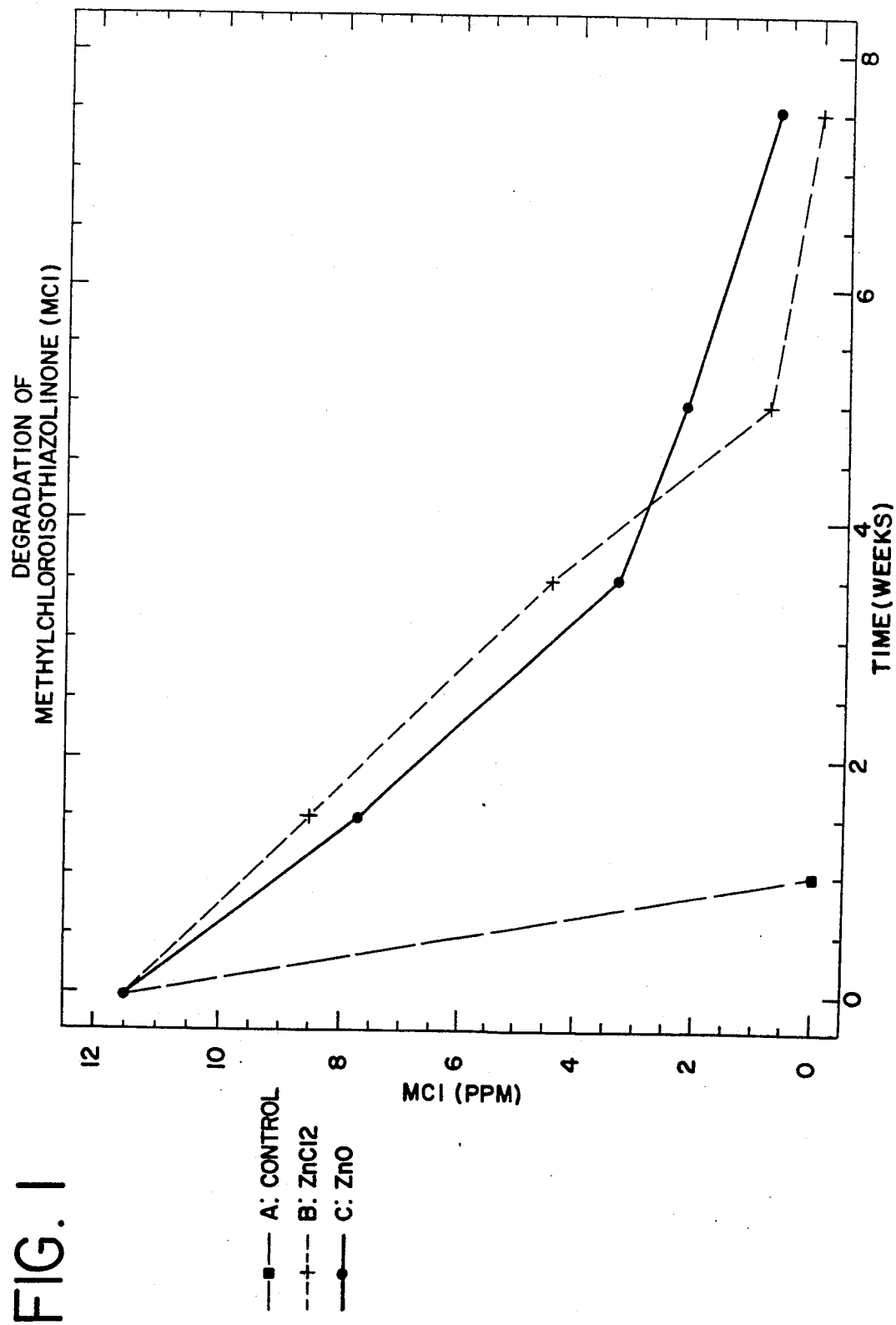
FIG. 1 is a graph showing the rate of degradation of the preservative, 5-chloro-2-alkyl-4-isothiazolin-3-one, over time, in one embodiment of an anti-dandruff shampoo containing zinc pyrithione. The graph compares the rate of degradation of the preservative when a stabilizer is added to when the stabilizer is not present.

In a first embodiment of the invention an aqueous anti-dandruff shampoo is provided comprising up to about 40% surfactants, from about 0.1% to about 2.0% zinc pyrithione, from about 1 to about 30 ppm of a preservative selected from the group consisting of 5-chloro-2-alkyl-4-isothiazolin-3-one, 2-alkyl-4-isothiazolin-3-one, and mixtures thereof, from about 0.001% to about 1.0% of a stabilizer comprising a zinc compound, miscellaneous optional ingredients; and water comprising the balance.

Surfactants useful in shampoos are well known to those skilled in the art and can include the anionic, nonionic, amphoteric and zwitterionic types. The surfactants are present at a level up to about 40%, preferably from about 4% to about 20%.

Anionic surfactants useful in the present invention include, but are not limited to, the alkali metal salts of organic reaction products having in their molecular structure an alkyl radical containing from 8-22 carbon atoms and a sulfonic acid radical. Examples of such anionic surfactants include the anionic sulfate surfactants having the general formula:

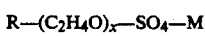

$$R-(C_2H_4O)_x-SO_4-M$$

wherein R is an alkyl group having from about 8 to about 18 carbon atoms; x is a number from 0 to about 4; and M is selected from the group consisting of monoethanolamine, diethanolamine, triethanolamine, ammonium, sodium and potassium. Sodium laureth sulfate, wherein x is 1, is most preferred.

The sulfate may be present at a level up to about 15%, preferably the sulfate is present at a level from about 2% to about 10%. More preferably, the sulfate is present at a level of about 5%.

Other anionic surfactants useful in the present invention are the $C_8-C_{18}$ acyl sarcosinates (e.g. sodium lauroyl sarcosinate). Sodium lauroyl sarcosinate is most preferred. The sarcosinate may be present at a level of up to about 15%, preferably from about 2% to about 10%. More preferably, the sarcosinate is present at a level of about 6%.

Zwitterionic surfactants useful in present invention include, but are not limited to, betaines having the general formula:

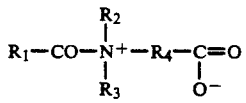

$$R_1-CO-\overset{R_2}{\underset{R_3}{N^+}}-R_4-\overset{C=O}{\underset{O^-}{|}}$$

wherein $R_1$ is an alkyl group containing about 10 to about 18 carbon atoms; and $R_2$, $R_3$, and $R_4$ are each $C_1-C_4$ alkyl. Preferably, the betaine is cocoamidopropyl dimethyl betaine.

The betaine may be present at a level up to about 5%, preferably from about 0.5% to about 3%. More preferably, the betaine is present at about 1.5%.

The nonionic surfactants useful in the present invention include, but are not limited to, the amide type of nonionic surfactants. For example, the nonionic surfactant includes the ammonia, monoalkanol, and dialkanol amides of fatty acids having an acyl moiety of from about 8 to about 18 carbon atoms where the alkanol has from 2 to 4 carbon atoms and is represented by the general formula:

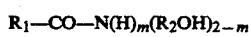

$$R_1-CO-N(H)_m(R_2OH)_{2-m}$$

wherein $R_1$ is a saturated or unsaturated aliphatic hydrocarbon radical having from 8 to 18, preferably from 12 to 14 carbon atoms; $R_2$ is a methylene, ethylene, or propylene group; and m is 0, 1, or 2, preferably 0 or 1, most preferably 0.

Thus, the amides that are useful in the present invention, include but are not limited to, the mono and diethanol coconut, lauric, and myristic fatty acid amides. The acyl moieties may be derived from naturally occurring glycerides, e.g., coconut oil, palm oil, soybean oil and tallow, but can be derived synthetically, e.g., by the oxidation of petroleum, or hydrogenation of carbon monoxide by the Fischer-Tropsch process.

The monoethanolamides and diethanolamides of $C_{12}$–$C_{14}$ fatty acids are preferred, particularly lauryldiethanolamide.

The amide may be present at a level of up to about 5%, preferably from about 1% to about 4%. More preferably, the amide is present at about 2%.

Pyrithione, pyrithione salts and dipyrithione have well-known anti-microbial properties. Zinc pyrithione is frequently used in preparing anti-dandruff shampoos. In the present invention, zinc pyrithione is present in the shampoo from about 0.1% to about 2%.

A preservative must be added to the shampoo composition to retard or prevent microbiological growth and thus prevent contamination of the shampoo. Preservatives useful in the present invention include the thiazolinones selected from the group consisting of 5-chloro-2-alkyl-4-isothiazolin-3-one, 2-alkyl-4-isothiazolin-3-one, and mixtures thereof. The alkyl is selected from the group consisting of methyl, ethyl, propyl, or butyl, and mixtures thereof. More preferably, the alkyl is methyl. Most preferably, the preservative is sold by Rohm & Haas under the trade name KATHON CG and is stated to contain 1.15%, by weight, of 5-chloro-2-alkyl-4-isothiazolin-3-one and 0.35%, by weight, of 2-alkyl-4-isothiazolin-3-one.

The preservative is added to the shampoo at a level of from about 1 ppm to about 30 ppm. Preferably, the preservative is added at a level of about 15 ppm.

As discussed above, the zinc pyrithione may react adversely with the preservative and reduce the activity of the preservative. Accordingly, an essential ingredient of the shampoo composition is a stabilizer for the preservative. Surprisingly, it has been found that the use of a zinc compound as a stabilizer reduces the degradation of a thiazolinone preservative. Preferably, the stabilizer is a zinc compound selected from the group consisting of: a zinc salt of an organic acid, a zinc salt of an inorganic acid, zinc oxide, zinc hydroxide, and mixtures thereof. For example, zinc acetate, zinc chloride, zinc sulfate, and the hydrates and ammoniates of zinc salts may be used. Zinc oxide and zinc hydroxide, which is a hydrated form of zinc oxide, may also be useful.

The stabilizer can be added to the shampoo composition at a level of about 0.001% to about 1%. Preferably, the stabilizer is added at a level from about 0.01% to about 0.1%.

Of course the shampoo can contain other well known miscellaneous optional ingredients such as humectants, conditioning agents, suspending agents, pH control agents, and fragrances and colors at a level of up to about 20%, preferably up to about 10%. For example, humectants such as aliphatic alcohols, glycol ethers, and mixtures thereof can be used. Examples of alcohols useful in the present invention are the lower $C_1$–$C_8$ mono-, di-, and tri-alcohols, such as ethanol, 1,2,3 propanetriol, and propylene glycol.

Conditioning agents such as panthenol and proteins such as hydrolyzed animal proteins are also beneficial. Suspending agents are known and include magnesium aluminum silicate and hydroxypropyl methylcellulose. Preferably, pH control agents such as phosphoric acid can be added so that the shampoo composition has a neutral to slightly acidic pH.

Water, preferably deionized or purified, comprises the balance.

In accordance with a more preferred embodiment, the shampoo consists essentially of up to about 40% of surfactants, from about 0.1% to about 2% zinc pyrithione, from about 1 to about 30 ppm of 5-chloro-2-methyl-4-isothiazolin-3-one, 2-methyl-4-isothiazolin-3-one, and mixtures thereof, from about 0.001 to about 1% of zinc chloride, and water comprising the balance.

In accordance with the most preferred embodiment, the shampoo consists essentially of about 1.5% of cocoamidopropyl dimethyl betaine, about 6% of sodium lauroyl sarcosinate, about 5% sodium laureth sulfate, about 2% of lauryldiethanolamide, about 1% of zinc pyrithione, abut 11.5 ppm of 5-chloro-2-methyl-4-isothiazolin-3-one and about 3.5 ppm of 2-methyl-4-isothiazolin-3-one, about 0.05% of zinc chloride, and water comprising essentially the balance.

The following examples are given to illustrate the invention.

EXAMPLE 1

The following aqueous shampoo can be prepared.

| COMPONENT | (% by weight) |
|---|---|
| Cocoamidopropyl dimethyl betaine (30% active) | 5 |
| Sodium lauroyl sarcosinate (30% active) | 20 |
| Sodium laureth sulfate (25% active) | 20 |
| Lauryldiethanolamide (100% active) | 2 |
| Zinc pyrithione (48% dispersion) | 2 |
| 5-chloro-2-methyl-4-isothiazolin-3-one | 11.5 ppm |
| 2-methyl-4-isothiazolin-3-one | 3.5 ppm |
| Zinc chloride | 0.05 |
| Miscellaneous Optional Ingredients | |
| Magnesium aluminum silicate | 1 |
| Hydroxypropyl methylcellulose | 1 |
| Methylparaben | 0.3 |
| Glycerin | 5 |
| Panthenol | 0.5 |
| Hydrolyzed animal protein | 0.5 |
| Water | q.s. to 100 |

EXAMPLE 2

The following aqueous shampoo compositions were prepared.

| COMPONENT | COMPOSITION (% by weight) | | |
|---|---|---|---|
| | A | B | C |
| Cocoamidopropyl dimethyl betaine (30% active) | 5 | 5 | 5 |
| Sodium lauroyl sarcosinate (30% active) | 20 | 20 | 20 |
| Sodium laureth sulfate (25% active) | 20 | 20 | 20 |
| Lauryldiethanolamide | 2 | 2 | 2 |
| Zinc pyrithione (48% dispersion) | 2 | 2 | 2 |
| 5-chloro-2-methyl-4-isothiazolin-3-one (ppm) | 11.5 | 11.5 | 11.5 |
| 2-methyl-4-isothiazolin-3-one (ppm) | 3.5 | 3.5 | 3.5 |
| Zinc chloride | — | 0.1 | — |
| Zinc Oxide | — | — | 0.07 |
| Miscellaneous Optional Ingredients | | | |

-continued

| COMPONENT | COMPOSITION (% by weight) | | |
|---|---|---|---|
| | A | B | C |
| Magnesium aluminum silicate | 1 | 1 | 1 |
| Hydroxypropyl methylcellulose | 1 | 1 | 1 |
| Methylparaben | 0.3 | 0.3 | 0.3 |
| Glycerin | 5 | 5 | 5 |
| Panthenol | 0.5 | 0.5 | 0.5 |
| Hydrolyzed animal protein | 0.5 | 0.5 | 0.5 |
| Water | q.s. to 100 | | |

Each of the compositions A, B, and C were analyzed over a period of time to determine the stability of the preservative 5-chloro-2-methyl-4-isothiazolin-3-one. As shown in FIG. 1, the addition of zinc chloride and zinc oxide, compositions B and C, respectively, decreased the rate degradation of the preservative to an acceptable level as compared to composition A which did not contain any stabilizer.

Of course, it should be understood that a wide range of changes and modifications can be made to the embodiments described above. It is therefore intended that the foregoing description illustrates rather than limits this invention, and that it is the following claims, including all equivalents, which define this invention.

I claim:

1. An aqueous anti-dandruff shampoo comprising:
   a. up to about 40% surfactants selected from the group consisting of anionic, nonionic, amphoteric and zwitterionic surfactants;
   b. from about 0.1% to about 2% zinc pyrithione;
   c. from about 1 to about 30 ppm of a preservative selected from the group consisting of 5-chloro-2-alkyl-4- isothiazolin-3-one, 2-alkyl-4-isothiazolin-3-one, wherein the alkyl is selected from the group consisting of methyl, ethyl, butyl, propyl and mixtures thereof;
   d. from about 0.001% to about 1% of a preservative stabilizer comprising a zinc compound selected from the group consisting of a zinc salt of an organic acid, a zinc salt of an inorganic acid, zinc oxide, zinc hydroxide, and mixtures thereof; and,
   e. water comprising the balance.

2. The anti-dandruff shampoo of claim 1 wherein the surfactant includes:
   a. up to about 5% of a betaine;
   b. up to about 15% of a sarcosinate;
   c. up to about 15% of a sulfate; and
   d. up to about 5% of an amide.

3. The anti-dandruff shampoo of claim 1 wherein the surfactant includes:
   a. up to about 5% of a betaine, wherein the betaine is cocoamidopropyl dimethyl betaine;
   b. up to about 15% of a sarcosinate, wherein the sarcosinate is sodium lauroyl sarcosinate;
   c. up to about 15% of a sulfate, wherein the sulfate is sodium laureth sulfate; and
   d. up to about 5% of an amide, wherein the amide is lauryldiethanolamide.

4. The anti-dandruff shampoo of claim 1 wherein the stabilizer is zinc chloride.

5. An aqueous anti-dandruff shampoo comprising:
   a. from about 4% to about 20% surfactants selected from the group consisting of anionic, nonionic, amphoteric and zwitterionic surfactants;
   b. from about 0.1% to about 2% zinc pyrithione;
   c. from about 1 to about 30 ppm of a preservative selected from the group consisting of 5-chloro-2-alkyl-4-isothiazolin-3-one, 2-alkyl-4-isothiazolin-3-one, and mixtures thereof, wherein the alkyl is methyl, ethyl, propyl, or butyl and which can be the same or different;
   d. from about 0.01% to about 0.1% of a preservative stabilizer comprising a zinc compound selected from the group consisting of a zinc salt of an organic acid, a zinc salt of an inorganic acid, zinc oxide, zinc hydroxide, and mixtures thereof; and, water comprising the balance.

6. The anti-dandruff shampoo of claim 5 wherein the surfactant includes:
   a. from about 0.5% to about 3% of a betaine;
   b. from about 2% to about 10% of a sarcosinate;
   c. from about 2% to about 10% of a sulfate; and
   d. from about 1% to about 4% of an amide.

7. The anti-dandruff shampoo of claim 5 wherein the surfactant includes:
   a. from about 0.5% to about 3% of a betaine, wherein the betaine is cocoamidopropyl dimethyl betaine;
   b. from about 2% to about 10% of a sarcosinate, wherein the sarcosinate is sodium lauroyl sarcosinate;
   c. from about 2% to about 10% of a sulfate, wherein the sulfate is sodium laureth sulfate; and
   d. from about 1% to about 4% of an amide, wherein the amide is lauryldiethanolamide.

8. The anti-dandruff shampoo of claim 5 wherein the stabilizer is zinc chloride.

9. An aqueous anti-dandruff shampoo consisting essentially of about 1.5% of cocamidopropyl betaine; about 6% of sodium lauroyl sarcosinate; about 5% sodium laureth sulfate; about 2% of lauryldiethanolamide; about 1% of zinc pyrithione; about 11.5 ppm of 5-chloro-2-methyl-4-isothiazolin-3-one; about 3.5 ppm of 2-methyl-4-isothiazolin-3-one; about 0.05% of a preservative stabilizer, the stabilizer being zinc chloride; about 1% of magnesium aluminum silicate; about 1% of hydroxypropyl methylcellulose; about 0.3% of methylparaben; about 4% of glycerin; and, water comprising the balance.

* * * * *